United States Patent [19]

Dorn

[11] 3,932,222
[45] Jan. 13, 1976

[54] FOR ISOLATING PATHOGENIC MICROORGANISMS

[75] Inventor: Gordon L. Dorn, Dallas, Tex.

[73] Assignee: J. K. & Susie L. Wadley Research Institute and Blood Bank, Dallas, Tex.

[22] Filed: Dec. 20, 1974

[21] Appl. No.: 535,148

[52] U.S. Cl............... 195/127; 128/218 M; 128/272
[51] Int. Cl.²............................................ C12K 1/04
[58] Field of Search................ 195/103.5, 127, 139; 128/218 M, 272; 210/DIG. 23

[56] References Cited
UNITED STATES PATENTS 3,875,012    4/1975    Dorn et al..................... 195/103.5 R Primary Examiner—Alvin E. Tanenholtz
Assistant Examiner—Robert J. Warden
Attorney, Agent, or Firm—Richards, Harris and Medlock

[57] ABSTRACT

A mixing and centrifugation device particularly suitable for use in procedures involving detection of microbial pathogens which includes an elongated enclosed centrifugation receptacle containing an evacuated space and having an injectable closure on an end thereof with an enclosed treating fluid chamber disposed in communication and adjacent the injectable closure and separated from the evacuated space by a thin rupturable membrane. A sample treating fluid is carried within the enclosed treating fluid chamber and a sterile aqueous solution having a greater density than a sample fluid but able to selectively receive microbial pathogens from the sample fluid is disposed within the evacuated chamber. A sample is deposited on the sterile aqueous solution via an injection needle by passing the injection needle through the injectable closure, the enclosed treating fluid chamber, and rupturing the thin membrane such that the sample treating fluid contacts the sample as it passes from the injection needle and is deposited on the liquid filter medium.

24 Claims, 8 Drawing Figures

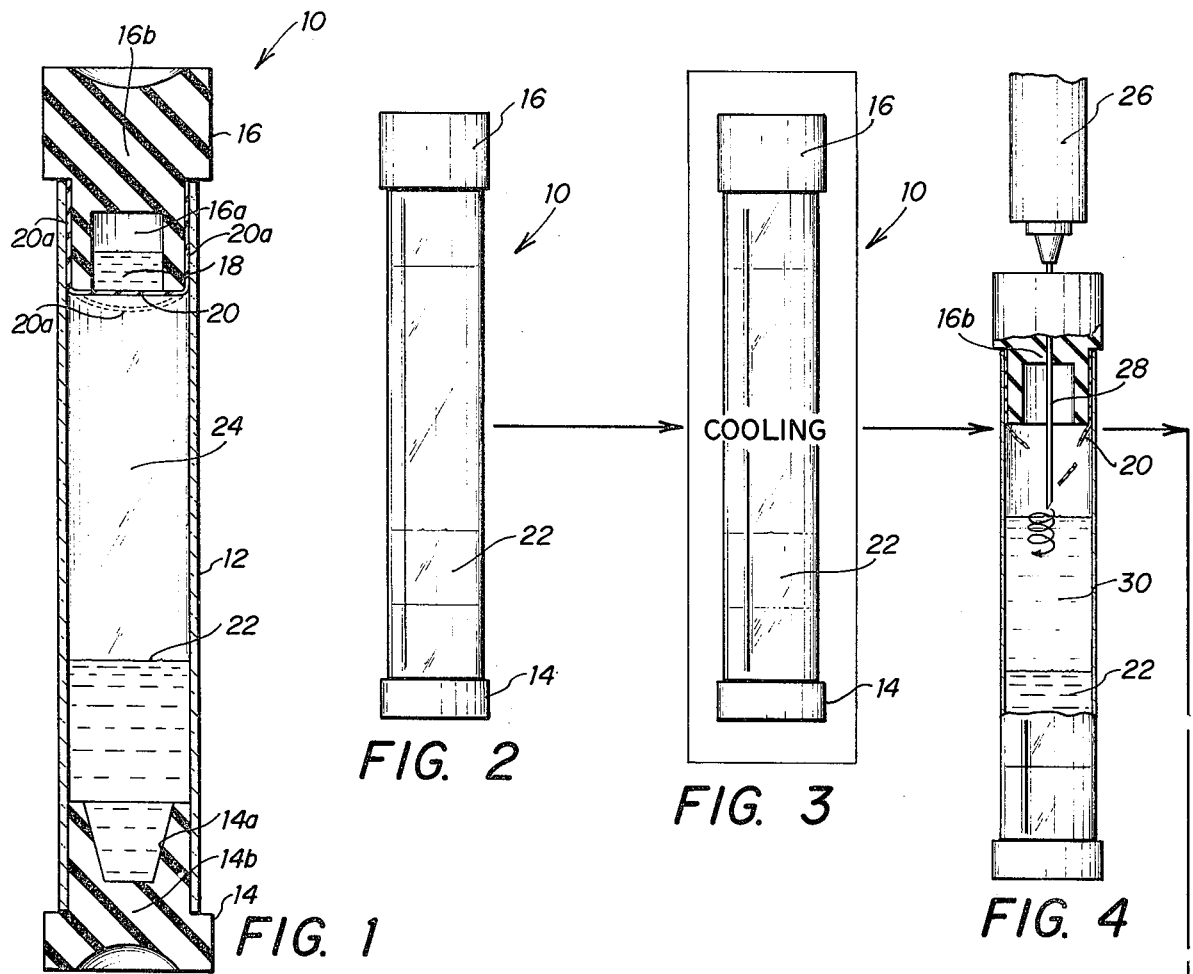
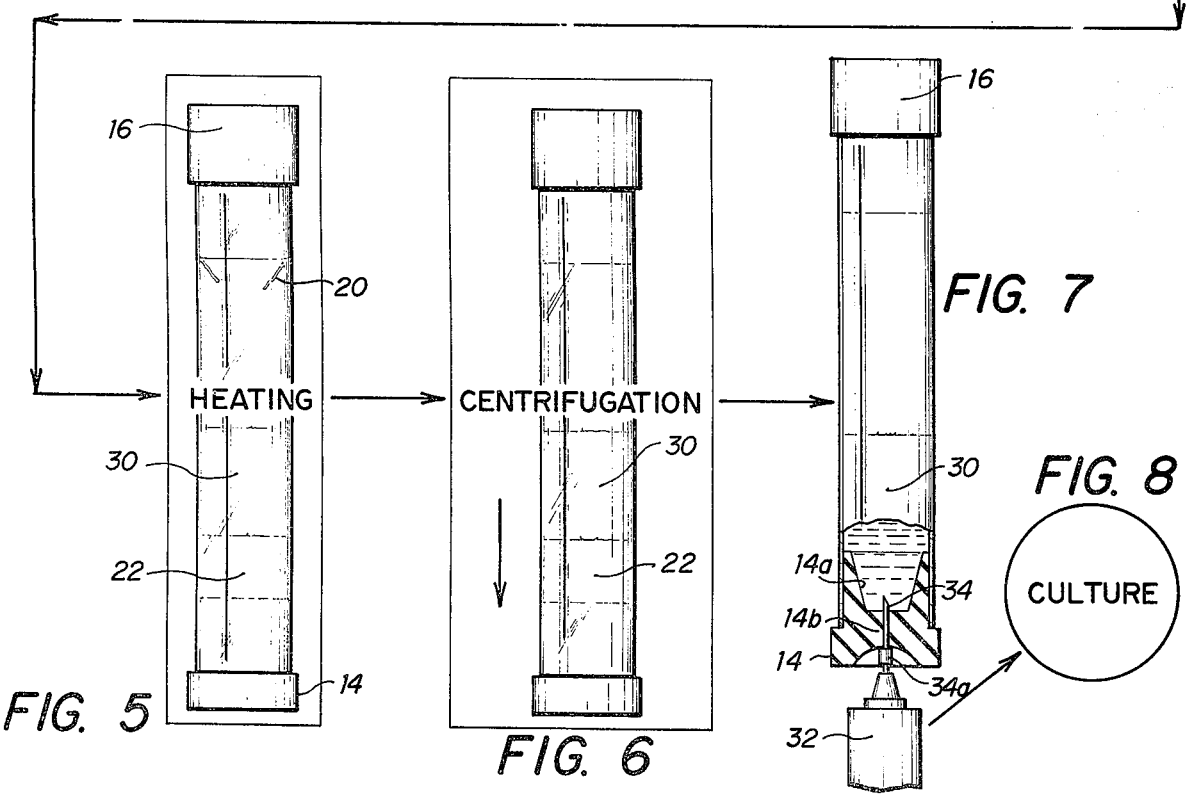

FOR ISOLATING PATHOGENIC MICROORGANISMS

BACKGROUND OF THE INVENTION

This invention relates to the detection of microbial pathogens. In another aspect, this invention relates to a novel device useful for mixing and centrifugation of fluid samples. In still another aspect, this invention relates to a novel device which is used for admixing a sample fluid containing microbial pathogens with a treating fluid and thereafter selectively extracting the microorganisms from the sample fluid. In still another aspect, this invention relates to a novel method and apparatus for diagnosing septicemia.

Septicemia which is the presence of pathogenic microorganisms in the blood is one of the most serious types of infection encountered. In spite of an armament of antibiotics and fungal drugs, the mortality rate from septicemia is approximately 25%. In addition, when shock accompanies septicemia, the mortality rate increases to over 60%. Patients who are suffering from debilitating diseases, undergoing major surgery, receiving immunosuppressive drugs, or anticancer medications are particularly prone to septicemia.

Early administration of appropriate antibiotic therapy is important in fighting septicemia. Consequently, it is imperative that the physician know as rapidly as possible not only whether the patient has septicemia, but also the identity of the infecting organisms, and the susceptibility of the microorganisms to antibiotic agents. Thus, the proper diagnosis of septicemia depends upon very rapid and efficient quantitative analysis of the patients blood. It is imperative during the quantitative analysis of the patients blood or other body fluid that the sample fluid not be contaminated with pathogens from the laboratory environment.

The conventional methods and equipment which are utilized to detect microorganisms in the blood sample suffer from one or more serious drawbacks which include a lengthy detection time, not being quantitative, and not able to detect the presence of different types of microbial pathogens within a sample, and being susceptible to contamination by laboratory atmosphere and personnel.

Recently, an improved method has been developed for determining the presence of microbial pathogens within a sample fluid which is extremely rapid and quantitative and minimizes contamination of the sample from the laboratory environment and personnel. This method is disclosed in copending U.S. Pat. application Ser. No. 428,135 filed Jan. 9, 1974, and entitled "DETECTION OF MICROBIAL PATHOGENS". According to this improved method for the detection of microbial pathogen, a sample of body fluid such as blood (preferably a lysed blood sample) is deposited upon a liquid filter medium within a confined sterile zone. The liquid filter medium has a density greater than the sample fluid and comprises a sterile aqueous solution which will selectively receive microbial pathogens from the sample fluid. Thereafter, the confined sterile zone is subjected to centrifugation to force the sample fluid against the liquid filter medium and cause the microbial pathogens to selectively pass therein and thereby separate from the mass of the body fluid sample. Next, the liquid filter medium containing the microbial pathogens is separated from the remainder of the sample fluid and portions of the liquid filter medium are subjected to culturing conditions. An improved apparatus for carrying out the novel method is disclosed in copending application Ser. No. 437,890 filed Jan. 30, 1974, and entitled "APPARATUS AND METHOD FOR THE DETECTION OF MICROBIAL PATHOGENS".

STATEMENT OF THE INVENTION

According to one embodiment of the subject invention, an improved mixing and centrifugation device is provided which comprises an elongated centrifugation tube containing an evacuated centrifugation chamber, and an injectable closure means on one end thereof which has an enclosed sample treating fluid chamber disposed in communication therewith and is separated from said evacuated centrifugation chamber by a thin rupturable membrane. A sample treating fluid is disposed within the treating fluid chamber. A sample is deposited into the centrifugation chamber by passing it through an injection needle which is inserted into the injectable closure means and through the thin rupturable membrane. The action of the injection needle will not only provide communication to the interior of the centrifugation chamber but will also rupture the thin rupturable membrane and cause the sample treating fluid to be automatically admixed with the sample as it is injected into the interior of the centrifugation chamber.

In accordance with a preferred embodiment of the subject invention, a liquid filter medium which has a greater density than the sample fluid to be deposited therein and which will selectively receive microbial pathogens from the sample fluid is positioned within the evacuated centrifugation chamber, and the second end of the centrifugation tube opposite the first end which contains said injectable closure means is sealed with a second injectable closure means.

In accordance with another preferred embodiment of the subject invention, the above described centrifugation and mixing apparatus is provided with a syringe means for removing the liquid filter medium from the evacuated chamber which includes a short stylus which is sufficiently long to only penetrate the thickness of the second injectable closure means and not to materially pass into said liquid filter medium when it is positioned thereon and furthermore wherein the thickness of the injectable closure means on said first end of said elongated centrifugation tube is longer than the length of said stylus to prevent accidental puncture of the first injectable closure means by the short stylus.

SHORT DESCRIPTION OF THE DRAWINGS

This invention can be more easily understood from a study of the drawings in which:

FIG. 1 is a section of a preferred mixing and centrifugation device of the subject invention; and FIGS. 2 through 8 are schematic illustrations depicting a process for detecting microbial pathogens by the use of the device of FIG. 1.

DETAILED DESCRIPTION OF THE INVENTION

The novel mixing and centrifugation device 10 of the subject invention is illustrated in cross-section in FIG. 1. As shown, the mixing and centrifugation device 10 comprises an elongated tubular centrifugation vessel 12, having an injectable closure member 14 which sealably closes the lower end thereof, and an injectable closure member 16 which sealably closes the upper end thereof.

Centrifugation vessel 12 can be made of glass or hard plastic such as polycarbonate or polypropylene. Injectable closure members 14 and 16 can comprise rubber self-sealing stoppers. The leading end of injectable closure member 14 carries a frustoconical recess 14a. Injectable web 14b forms the bottom of the frustoconical recess 14a. The leading end of injectable closure member 16 carries a recess 16a. Injectable web 16b is preferably of greater thickness than injectable web 14b as will be described in detail hereinbelow in connection with the description of FIGS. 2 through 8.

Recess 16a of injectable closure 16 functions as a sample treating fluid chamber and contains a sample treating composition 18. The sample treating composition 18 is retained within recess 16a by thin rupturable membrane 20. Rupturable membrane 20 is made of a thin elastomeric material such as natural rubber or an artifical rubber which is stretched over the opening of recess 16a. As shown in the embodiment in FIG. 1, the rupturable membrane 20 is stretched over the opening of recess 16a and is of sufficient length so that it overlaps the sidewalls of injectable closure member 16 by overlaps 20a. Thus overlaps 20a are held in interference fit between the outer sidewalls of injectable closure member 16 and the inner sidewalls of tubular centrifugation vessel 12. Rupturable member 20 can conveniently have a thickness which corresponds to that of a toy balloon, for example. In general, rupturable membrane 20 can be made of any suitable material which will effectively separate sample treating composition fluid 18 from the interior of evacuated space 24 but yet will split, fragment, disintegrate or otherwise loose its sealed configuration over the mouth of recess 16a when pierced by a sharp object, i.e., a hypodermic needle and allow sample treating composition 18 to enter evacuated space 24. Thus, thin elastomeric materials which are stretched in tension are generally preferred for use as rupturable membrane 20.

The sterile contents of centrifugation vessel 12 comprise a liquid filter medium 22 and an evacuated space 24 which may be a complete or a partial vacuum. Evacuated space 24 is maintained at a lower than atmospheric pressure at a predetermined value so that the centrifugation vessel can receive a known amount of liquid by injection through injectable closure member 16 without excessive pressure being built up within the interior thereof which would cause injectable closure members 14 and 16 to become dislodged from the openings within centrifugation vessel 12.

The liquid filter medium 22 can be any of the liquid filter media set forth in said copending patent application for detecting microbial pathogens and generally, comprises an aqueous solution of any solute which is nontoxic to the microbial organisms being suspended, and has a density sufficiently high to suspend red and white blood cells or blood cell debris. The solute is preferably nonionic. Thus, the liquid filter medium has a density greater than blood, e.g., greater than about 1.06 gm/cc, and will suspend blood cells or blood cell debris, but yet will receive microbial pathogens. In addition, the liquid filter medium preferably contains a minor amount of a thermally sensitive gelling agent.

Suitable solutes which can be used in the liquid filter medium 22 include the sugars such as sucrose, glucose, maltose, fructose, manitol, sorbitol, and the like. Generally, liquid filter medium 22 should be at least about 40 weight percent of the sugar and can contain the sugar up to the saturation limit thereof. Preferably, the sugars are contained within liquid filter medium 22 in the range of from about 40 to about 50 weight percent thereof. Generally, the sugars, and especially sucrose, are preferred solutes for liquid filter medium 22 because the liquid filter medium can be maintained at a physiological pH, i.e., 6.0–7.0 and when combined with gelatin, they can be autoclaved.

Any solute can be used in the scope of this invention so long as the resulting solution is more dense than red blood cells and red blood cell debris, and is nontoxic to the microbial pathogens. Other suitable such materials include a chemical commonly known as Hypaque sodium, $C_{11}H_8I_3N_2NaO_4$ (3,5-diacetamido-2,4,6-triiodobenzoic acid sodium salt). This material can be utilized in aqueous solution in the same concentration as the sugar as described above. Another class of solutes which can be used to form the aqueous liquid filter medium in the scope of the subject invention includes macromolecular solutes which are capable of producing a liquid gel structure in aqueous media which have a pore size small enough to preclude red cells or red cell debris but large enough to pass microbial pathogens.

An example of a suitable such macromolecular solute is a water soluble crosslinked polymer having microporous openings throughout its solubilized network. A suitable such water soluble polymer includes a copolymer of sucrose and epichlorohydrin which has a weight average molecular weight in the range of from about 30,000 to about 500,000, and an intrinsic viscosity of about 0.17dl/g, a specific rotation $[\alpha]_D^{20}$ of $+56.5°$ and contains dialyzable material in an amount of less than 1 weight percent. A suitable such polymer is sold under the trademark of "FICOLL" by Pharmacia Fine Chemicals, Inc., 800 Centennial Avenue, Piscastaway, New Jersey. Another such polymer which can be used in the scope of this invention is dextran, having a weight average molecular weight in the range of about 10,000 to about 2,000,000 and preferably about 50,000. These polymers, when dissolved in water in accordance with the subject invention function as a liquid filter medium for microbial pathogens and apparently have microporous openings throughout their solubilized network in the range of from about 1 micron to about 7 microns.

The water soluble polymer or macromolecular solute is preferably present in the aqueous solution in the range of from about 10 to about 40 weight percent and more preferably from about 20 to about 30 weight percent thereof.

It is to be understood that the term "thermally sensitive gelling agent" is meant any agent which will gel the aqueous solution of filter medium 22 at a temperature generally lower than room temperature but yet will liquefy at higher temperatures which are nondeleterious to the microbial pathogens, e.g., lower than about 50°C and generally no higher than about 42°C. Suitable thermosensitive gelling agents include any such gelling agent which is nondeleterious to the solution or to the sample being analyzed. Examples of suitable such materials include gelatins, i.e., the proteins obtained from collagen by boiling skin, ligaments, tendons, bones, and the like in water. Any suitable amount of thermally sensitive gelling agent can be utilized, e.g., about 0.5 to about 5 weight percent of filter medium 22.

In addition, in accordance with a preferred embodiment of the subject invention an oxygen scavenger and/or oxygen sensitive dye are included within the liquid filter medium. The presence of the oxygen scavenger will assure that the interior of the mixing and centrifugation device 10 is maintained at an anaerobic environment. More specifically, the medical profession is concerned about anaerobic bacterial infections of the human body. If the test for isolating and detecting microbial pathogens is carried out in aerobic environment, then it is quite apparent that the anaerobic bacteria will not be detected. Therefore, the presence of a minor effective amount of a reducing agent (a conventional oxygen scavenger) is utilized within the liquid filter medium 22 in the scope of a preferred embodiment of the subject invention. Reducing agents which can be used in the scope of the subject invention include L-cystine, sodium thioglycolate, ascorbic acid and the like. The preferred reducing substance which is used in the liquid filter medium 22 in the scope of the subject invention is a mixture of L-cystine and sodium thioglycolate. Furthermore, it is within the scope of a preferred embodiment of the subject invention to include a minor effective quantity of an oxygen sensitive dye in the liquid filter medium. The dye can be utilized either in the presence or the absence of the above disclosed reducing agent. The dye is preferably colorless in the absence of oxygen, but changes color when contact is made with oxygen. Thus a color change indicates that oxygen is present within the interior of the mixing and centrifugation device 10 which indicates the loss of the vacuum within the interior thereof. Suitable oxygen sensitive dyes which can be used in the scope of this invention include resazurin and methylene blue. Any other oxygen sensitive dye which is nondeleterious to the liquid filter medium 22 and the microbial separation process carried out within the interior of mixing and centrifugation device 10 can be used in the scope of the subject invention. A typical liquid filter medium which is used in the scope of the subject invention is as follows:

50% (w/w) sucrose
1.5% (w/w) gelatin
0.05% (w/v) L-cystine
0.05% (w/v) sodium thioglycolate
0.0001 – 0.0002% (w/v) resazurin
pH to 6.0

Generally, the reducing agent can comprise from about 0.01 to about 0.2% by weight of the liquid filter medium and the oxygen sensitive dye can comprise from about 0.001 to about 0.0005% by weight of the liquid filter medium.

Treating composition 18 can contain any suitable ingredient or ingredients with which it is desired to treat the sample fluid before microbial pathogens are separated therefrom. In accordance with a specific embodiment of the subject invention, treating composition 18 comprises an aqueous solution of a lysing agent for blood. Any suitable lysing agent can be utilized in the aqueous solution which is nontoxic to microorganisms. A suitable such lysing agent is a nontoxic aqueous solution of saponin. It must be noted that many saponins are thought to be toxic to microbial pathogens. However, as set forth in copending application Ser. No. 423,447, filed Dec. 10, 1973, entitled "DETOXIFICATION OF SAPONINS", which is herein incorporated by reference into this application, a new method is disclosed for removing the toxic ingredients from the heretofore thought to be toxic saponins. In general, the toxic saponin material can be detoxified in accordance with the invention set forth in this copending patent application and the resulting purified material used in the scope of this invention. In addition, the aqueous solution can contain an anticoagulant and/or an oxygen scavenger. A preferred anticoagulant is sodium polyanethol sulfonate (SPS) or Heparin, for example. Sodium polyanethol sulfonate is preferred because it not only acts as an anticoagulant but also inhibits the phagocytic activity of granulocytes and monocytes and the normal antibacterial activity of serum.

Mixing and centrifugation device 10 provides a convenient, inexpensive and practical way in which to combine a sample fluid such as blood with a sample treating solution such as set forth above prior to removal of the microbial pathogens which may be present from the sample fluid. More specifically, the sample can be deposited on the liquid filter medium 22 by passage through an injection needle which is inserted through web 16b, and membrane 20. The passage of an injection needle through membrane 20 which is stretched taut causes the membrane 20 to rupture and the sample treating composition 18 to be deposited within the interior of evacuated space 24 as the sample is passed thereto via the injection needle. This eliminates the necessity of having to premix the sample with the sample treating composition in a separate operation thus avoiding the possibility of additional risk of contamination. In addition, it has been found that some of the liquid filter media are incompatible with some of the pretreating agents such as lysing agents set forth above. Therefore, it is not possible to combine the sample treating fluid and the liquid filter medium within the interior of mixing and centrifugation device 10 for long periods of time. Thus, rupturable membrane 20 functions not only to separate the sample treating composition 18 from the liquid filter medium 22 but to rapidly release the sample treating composition 18 when its use is desired in the microbial pathogen detection process. It is not necessary that rupturable membrane 20 be a gas impermeable membrane but only that it be sufficiently impermeable to prevent passage of either the sample treating composition 18 or liquid filter medium 22 therethrough. More specifically, rupturable membrane 20 can be made of any conventional elastomeric material such as natural rubber and artifical elastomers such as for example polyisoprene. In addition, rupturable membrane 20 can be attached to the opening of recess 16a by any suitable means. It is preferable that rupturable membrane 20 be in the nonrelaxed or stretched state when positioned over recess 16a so that it will rupture when pierced by the point of the injection needle. Thus, rupturable membrane 20 serves as a barrier which is impermeable to the sample treating composition 18 and to the liquid filter medium 22, and it is sufficiently flexible to allow gas expansion within the sample treating solution chamber (recess 16a) because of a change in temperature and/or the presence of the vacuum within evacuated space 24. This flexibility is illustrated in broken line at 20a in FIG. 1 which shows rupturable membrane 20 in an extended position.

Now referring to FIGs. 2 through 8, the use of mixing and centrifugation device 10 will be described in relation to a procedure for the detection of microbial pathogens. Liquid filter medium 22 can comprise 1.5 milliliters of an aqueous solution containing 3.0 parts by weight of gelatin, 97.0 parts by weight water, 100.0 parts by weight sucrose, 0.8 parts by weight L-cystine, 0.8 parts by weight sodium thioglycolate, and 0.003 parts by weight resazurin, for example.

Sample treating solution 18 can contain any suitable constituent such as a lysing agent and/or anticoagulant and, if desired, an oxygen scavenger or reducing agent in any desirable concentration. Any amount of an anticoagulant which is sufficient for the amount of blood sample and any amount of lysing agents sufficient to lyse the blood sample, can be used. For example, 0.3 milliliters of an aqueous solution containing about 12% by weight of non-toxic saponin and about 2% by weight sodium polyanethol sulfonate can be used as sample treating composition 18. Initially, the mixing and centrifugation apparatus 10 is placed in an upright position as illustrated in FIG. 2 to allow the liquid filter medium 22 to pass downwardly against injectable closure member 14. Next, mixing and centrifugation device 10 is placed in a suitable cooling unit such as a refrigerator and is chilled sufficiently to cause the gelatin to solidify the liquid filter medium 22. For example, mixing and centrifugation device 10 can be chilled to 4°C. This step is illustrated in FIG. 3. Next a sample fluid such as a blood sample (e.g., 8 ml) is obtained with syringe 26 which carries hypodermic needle 28. Hypodermic needle 28 is then inserted through web 16b, the sample treating composition 18 within recess 16 a, and through rupturable membrane 20 causing it to rupture and the sample treating composition 18 to fall within evacuated space 24. The blood sample is then injected within the interior of mixing and centrifugation device 10 in a manner schematically illustrated in FIG. 4. The turbulence caused by the blood passing into evacuated space 24 will not disturb the liquid filter medium 22 which will remain as a solid bottom layer as illustrated in FIG. 4. Furthermore, the turbulence caused by the blood being injected into evacuated space 24 will result in a thorough admixing of the sample treating composition 18 and the blood sample to form the resulting mixture 30.

The mixing of the blood sample with sample treating composition 18 containing the lysing agent will result in the red blood cells becoming lysed which will therefore minimize the possible trapping effect of erythrocytes. This trapping effect would in general comprise the erythrocytes or lymphocytes becoming stacked on the top of the liquid filter medium during the centrifugation step and the stacked cells trapping microbial pathogens as they are passed downwardly during centrifugation and thereby preventing such pathogens from reaching the liquid filter medium. Furthermore, the sodium polyanethol sulfonate within the sample treating composition 18 acts as anticoagulant and inhibits the phagocytic activity of granulocytes and monocytes and the normal antibacterial activity of the serum once it becomes admixed with the blood sample.

Next, hypodermic needle 28 is withdrawn from injectable closure member 16 and the mixing and centrifugation device 10 containing the congealed liquid filter medium 22 and the blood sample admixed with treating composition 18 and illustrated as mixture 30 in FIGS. 4 and 5 is heated while in the upright position sufficiently to melt the gelatin and cause the liquid filter medium 22 to liquefy. Mixing and centrifugation device 10 is heated to a temperature which will not destroy any microbial pathogens which may be present in the blood sample but which will be sufficient to liquefy the gelatin. For example, while in the position as illustrated in FIG. 5, mixing and centrifugation device 10 can be heated by immersion in a water bath to a temperature set at about 37°C–42°C. The liquefaction of the gelatin within the liquid filter medium 22 yields a liquefied solution which is now ready to function as a filter medium for the microbial pathogens.

The separation of the microbial pathogens from the remaining portion of the blood sample is accomplished by placing mixing and centrifugation device 10 into a suitable centrifugation apparatus and subjecting it to sufficient centrifugal force to separate the microbial pathogens from the remaining constituents in the blood sample. The speed and time of centrifugation can vary widely depending upon the strength of the material of which centrifugation vessel 12 is made and the type of centrifugation apparatus. The centrifugation can be conveniently accomplished by imparting between about 100 and about 6000 gravities and preferably from about 1400–5000 gravities to mixing and centrifugation device 10. A suitable method includes a swinging bucket centrifuge rotor which imparts between about 2000 and 4000 gravities for 10 to about 20 minutes to the particular system described in this preferred embodiment. The centrifugation step is illustrated schematically in FIG. 6 below.

After mixing and centrifugation device is subjected to the centrifugation step as described above, a sterile syringe 32 carrying a shortened hypodermic needle 34 is passed through injectable web 14b of injectable closure member 14 as illustrated in FIG. 7. As illustrated, hypodermic needle 34 carries a stop 34a which will only allow the needle 34 to pierce injectable web 14b and the beveled end of needle 34 to extend into liquid filter medium 22 adjacent the end of frustoconical recess 14a. After this is accomplished, syringe 32 withdraws liquid filter medium 22 from the interior of mixing and centrifugation device 10 to leave the residual of the sample solution mixture 30 therewithin. It is noted that the length of the needle 34 is such that it cannot completely pierce web 16b of injectable closure member 16. This will assure that accidental puncture and loss of vacuum and entry into the sterile interior of mixing and centrifugation vessel 10 cannot occur by the short needle 34.

Furthermore, it is noted that in an alternate lesser preferred embodiment, a longer hypodermic needle can be utilized with syringe 32 and the needle can be passed to the interior of mixing and centrifugation device 10 to a point slightly past the interface between liquid filter medium 22 and the sample fluid mixture 30 initially removed from the tube. In this instance, the syringe should intially have the plunger retracted and be filled with sterile air in order that the sterile air can be pumped into the interior of the mixing and centrifugation device 10 incrementally as the sample layer is displaced. Thereafter, the liquid filter medium 22 can be removed.

Liquid filter medium 22 withdrawn by syringe 32 is next preferably agitated such as by shaking to cause the microbial pathogens to become thoroughly admixed and generally uniformly distributed therein. The liquid filter medium 22 containing the dispersed microbial pathogens is then distributed on suitable bacterial growth media in the culture step which is schematically depicted as FIG. 8 in the drawing. Suitable such growth media are set forth in said copending application entitled "DETECTION OF MICROBIAL PATHOGENS".

For example, with 1½ milliliters of liquid filter medium containing microbial pathogens, one blood agar plate can receive 0.2 milliliters of the medium and the plate can be incubated at 37°C in an aerobic atmosphere. Another blood agar plate can receive 0.2 milliliters of the aqueous solution and can be incubated at 37°C in a candle jar. Another blood agar plate can receive 0.2 milliliters of the aqueous solution and can be incubated at 37°C in an anaerobic environment. Another 0.2 milliliters of the solution can be placed on a sabouraud agar plate and incubated at 25°C in an aerobic environment. Another 0.2 milliliters of the solution can be placed on a EMB plate (Eosin methylene blue dye) plate and incubated at 37°C in a candle jar. Another 0.5 milliliters of the solution can be placed in a liquid thioglycolate medium and incubated at 37°C. The growth media can be checked daily for the presence of colonies. The number of microbial pathogens in 1 milliliter of blood can be determined by multiplying the number of colonies by a correction factor. This correction factor takes into consideration the recovery rate for a given organism, the volumes of blood and liquid filter solutions employed and the amount of final mixture plated. In the general example set forth above, the correction factor is 1.56.

It is noted that mixing and centrifugation device 10 as illustrated in the drawing is a preferred embodiment which is utilized in the scope of the subject invention for carrying out the separation of microbial pathogens from samples of body fluid. However, suitable mixing and centrifugation devices of the subject invention can have slightly different configurations. For example, it is within the scope of the subject invention to include an injectable closure means containing a recess 16a and a thin rupturable membrane thereover in one end of an elongated centrifugation tube having an integrally closed opposite end, i.e., a test tube. This will allow a sample fluid to be injected within the interior of the evacuated space within the tube and automatically mixed with the treating fluid by the action schematically depicted in FIG. 4. In this manner, various types of sample treating fluids can be admixed with various other types of sample fluids in a one step operation. In such cases, a second fluid, if desired, can be contained within the test tube portion of the device such that when a sample is injected within the device, it is automatically admixed with two different fluids which may be incompatible if stored together. Thus, while this invention has been described in relation to its preferred embodiments, it is to be understood that various modifications thereof will not be apparent to one skilled in the art from reading this specification and it is intended to cover such modifications as fall within the scope of the appended claims.

I claim:

1. A fluid mixing device comprising:
   a. an enclosed vessel having a first end and a second end and comprising a chamber containing an evacuated space maintained at a lower than atmospheric pressure;
   b. an injectable closure means sealably closing said first end of said enclosed vessel;
   c. an enclosed treating fluid chamber disposed in communication with said injectable closure means and separated from said evacuated chamber by an elastomeric film which will rupture when pierced by a needle; and
   d. a treating fluid disposed within said treating fluid chamber.

2. The fluid mixing device of claim 1 wherein said elastomeric film is stretched in tension.

3. The fluid mixing device of claim 2 wherein said injectable closure means comprises a tubular insert positioned within said first end of said enclosed vessel and an injectable web enclosing the outer end of said tubular insert, and the inner end of said tubular insert within said vessel having said elastomeric film stretched thereover to thereby form said treating fluid chamber within said tubular insert.

4. The device of claim 3 wherein the periphery of said elastomeric film is retained in an interference fit between the inner sidewall of said first end and the outer sidewall of said tubular insert.

5. A centrifugation and mixing device comprising;
   a. an enclosed elongated centrifugation vessel having a first end and a second end and comprising a chamber containing an evacuated space maintained at a lower than atmospheric pressure;
   b. first injectable closure means sealably closing said first end of said centrifugation vessel;
   c. a second injectable closure means sealably closing said second end of said centrifugation vessel; and
   d. an enclosed sample treating agent chamber containing a sample treating agent and disposed in communication with said first injectable closure means and separated from said chamber by an elastomeric film which will rupture when pierced by a needle.

6. The device of claim 5 wherein said elastomeric film is stretched in tension.

7. The device of claim 6 wherein said first injectable closure means comprises a tubular insert positioned within said first end of said centrifugation vessel and an injectable web enclosing said tubular insert, said tubular insert having said film stretched over the leading open end thereof thereby forming said sample treating agent chamber therewithin.

8. The device of claim 7 wherein the periphery of said elastomeric film is retained in an interference fit between the inner sidewall of said first end and the outer sidewall of said tubular insert.

9. The device of claim 7 wherein said second injectable closure means comprises an injectable web sealably closing said second end of said centrifugation vessel, and wherein the thickness of the injectable web of said first injectable closure means is greater than the thickness of the injectable web of said second injectable closure means.

10. The device of claim 9 in combination with a syringe for removing fluid therefrom having a stylus which is longer in length than the thickness of said injectable web of said second injectable closure means but shorter in length than the thickness of said injectable web of said first injectable enclosure means.

11. A device used for the isolation and concentration of microbial pathogens from a sample fluid comprising:
   a. an enclosed centrifugation vessel having a first end and a second end and containing an evacuated space maintained at a lower than atmospheric pressure adjacent a sterile liquid filter medium which is nontoxic to said microbial pathogens and has a greater density than the sample fluid but able to selectively receive microbial pathogens from said sample fluid;
   b. first injectable closure means sealably closing said first end of said elongated centrifugation vessel;
   c. second injectable closure means sealably closing the second end of said elongated centrifugation vessel; and d. an enclosed sample treating agent chamber containing a sample treating agent disposed in communication with said first injectable closure means and separated from said evacuated space by an elastomeric film which will rupture when pierced by a needle.

12. The device of claim 11 wherein said elastomeric film is stretched in tension.

13. The device of claim 12 wherein said first injectable closure means comprises a tubular insert positioned within said first end of said centrifugation vessel and an injectable web enclosing the outer end of said tubular insert, said tubular insert having said film stretched over the inner end thereof thereby forming said sample treating agent chamber therewithin.

14. The device of claim 13 wherein the periphery of said elastomeric film is retained in an interference fit between the inner sidewall of said first end and the outer sidewalls of said tubular insert.

15. The device of claim 11 wherein said liquid filter medium contains a minor effective amount of a thermally sensitive gelling agent.

16. The device of claim 15 wherein said minor effective amount of said thermally sensitive gelling agent is from about 1 to about 5 wt % of said liquid filter medium.

17. The device of claim 16 wherein said thermally sensitive gelling agent is gelatin.

18. The device of claim 15 wherein said liquid filter medium is an aqueous solution of a sugar.

19. The device of claim 18 wherein said sugar is sucrose.

20. The device of claim 19 wherein said aqueous solution contains at least 40 wt % of said sucrose.

21. The device of claim 15 wherein said liquid filter medium further contains a material selected from reducing agents and oxygen sensitive dyes and mixtures thereof.

22. The device of claim 15 wherein said liquid filter medium is an aqueous solution of a macromolecular solute having microporous openings throughout its solubilized network, said openings being of sufficient size to selectively pass said pathogens from said sample fluid.

23. The device of claim 22 wherein said polymer is epichlorohydrin-sucrose polymer having a molecular weight in a range of from about 300,000 to about 500,000 and a specific rotation $[\alpha]_D^{20}$ of $+56.5°$.

24. The device of claim 22 wherein said polymer is dextran having a molecular weight of from about 10,000 to about 2,000,000.

* * * * *

UNITED STATES PATENT OFFICE
CERTIFICATE OF CORRECTION

Patent No. 3,932,222          Dated January 13, 1976

Inventor(s)  Gordon L. Dorn

It is certified that error appears in the above-identified patent and that said Letters Patent are hereby corrected as shown below:

Col. 2, line 55 [Pg. 5, line 23], "section of a" should be --sectional view of a--.

Signed and Sealed this eighteenth Day of May 1976

[SEAL]

Attest:

RUTH C. MASON
Attesting Officer

C. MARSHALL DANN
Commissioner of Patents and Trademarks